United States Patent
McDonald et al.

(10) Patent No.: US 6,631,719 B2
(45) Date of Patent: Oct. 14, 2003

(54) LIGHTWEIGHT PATIENT OXYGEN DELIVERY SYSTEM

(75) Inventors: Lee McDonald, Ontario (CA); Maurice Lavimodiere, Ontario (CA)

(73) Assignee: Southmedic Incorporated (CA)

( * ) Notice: Subject to any disclaimer, the term of this patent is extended or adjusted under 35 U.S.C. 154(b) by 53 days.

(21) Appl. No.: 09/849,863

(22) Filed: May 4, 2001

(65) Prior Publication Data

US 2001/0042547 A1 Nov. 22, 2001

Related U.S. Application Data

(63) Continuation-in-part of application No. 09/572,637, filed on May 17, 2000, now Pat. No. 6,450,166.

(51) Int. Cl.[7] .............................................. A62B 18/00
(52) U.S. Cl. .............................. 128/207.11; 128/206.27
(58) Field of Search ................. 128/207.11, 200.24, 128/200.28, 201.22, 201.23, 201.18, 201.19, 204.18, 206.21, 206.28, 207.13, 207.18, 206.27, 206.26; D14/206, 137, 138; 379/420.01, 420.04

(56) References Cited

U.S. PATENT DOCUMENTS

| | | | |
|---|---|---|---|
| 4,593,688 A | | 6/1986 | Payton |
| D344,730 S | * | 3/1994 | Gattey et al. ............... D14/206 |
| D346,802 S | * | 5/1994 | Sacherman et al. ......... D14/206 |
| 5,457,751 A | * | 10/1995 | Such .......................... 381/375 |
| 5,575,282 A | | 11/1996 | Knoch et al. |
| 5,697,363 A | * | 12/1997 | Hart ....................... 128/201.19 |
| D410,921 S | * | 6/1999 | Luchs et al. ................ D14/142 |
| 6,065,473 A | | 5/2000 | McCombs et al. |
| 6,130,953 A | * | 10/2000 | Wilton et al. ................ 379/430 |
| 6,178,251 B1 | * | 1/2001 | Luchs et al. ................ 381/362 |
| D443,870 S | * | 6/2001 | Carpenter et al. .......... D14/206 |
| 6,247,470 B1 | * | 6/2001 | Ketchedjian ........... 128/200.28 |
| D449,883 S | * | 10/2001 | McDonald et al. ......... 381/364 |
| D451,598 S | * | 12/2001 | McDonald et al. ........ D24/110 |
| 6,373,942 B1 | * | 4/2002 | Braund ....................... 379/430 |
| D457,155 S | * | 5/2002 | Skulley et al. ............. D14/206 |
| 6,450,166 B1 | * | 9/2002 | McDonald et al. .... 128/206.27 |
| 6,496,589 B1 | * | 12/2002 | Pham et al. ................ 381/375 |

* cited by examiner

*Primary Examiner*—Weilun Lo
*Assistant Examiner*—Teena Mitchell
(74) *Attorney, Agent, or Firm*—Nikolai & Mersereau, P.A.

(57) ABSTRACT

A lightweight oxygen delivery system for a patient comprising a curved resilient headband to extend from side to side over a patient's head and to be comfortably seatably engaged thereon. A clip is secured towards one end of the headband. An elongated tubular boom is secured at one end to the clip to extend and hold its position, when in operation from said one end at the clip to another end located at a space in front of, and proximal to the patient's nose and mouth. An oxygen diffuser port is located at the other end of the boom, to deliver oxygen from the boom to the space in the vicinity of the patient's nose and mouth. The clip is constructed so as to hold securely an oxygen delivery tube from an oxygen source in fluid communication with said one end of the boom so as to deliver oxygen from the source to the boom for discharge through the diffuser, the tubular boom is secured within the sleeve for telescopic, longitudinal adjustment of the boom with respect to the sleeve to facilitate positioning of the oxygen diffuser with respect to the patient's nose and mouth.

17 Claims, 4 Drawing Sheets

LIGHTWEIGHT PATIENT OXYGEN DELIVERY SYSTEM

HISTORY OF THE APPLICATION

The present application is a continuation-in-part of Applicant's application Ser. No. 09/572,637 filed May 17, 2000, now U.S. Pat. No. 6,450,166.

BACKGROUND OF THE INVENTION

The present invention relates to a novel system for delivery of oxygen to a patient, and more particularly relates to a device which can be used to replace conventional oxygen masks and nose cannula oxygen delivery systems.

Mask oxygen therapy has been around for a very long time and has seen virtually no changes. Problems encountered with this style of therapy are well known but unavoidable using the mask as it is supplied today. A number of vendors supply oxygen masks as a commodity item, with the result that there has been little or no improvement in the technology because of the low profit margins accompanying the sale of such masks.

Conventional oxygen masks comprise tent like structures which are strapped over the nose and mouth of a patient, often using an elastic band or bands behind the patient's ears or head. Oxygen is fed from a supply through a tube into the bottom portion of the mask at the front of the patient.

Common problems with the mask include:
1. Some patients find it claustrophobic.
2. Many patients cannot tolerate the smell of plastic resin.
3. Patients must take the mask off to speak or eat thereby discontinuing therapy.
4. Some patients are allergic to the elastic (latex allergy).
5. Some patients feel ill when they wear an oxygen mask, (the psychological effect is truly remarkable on the patient and the patient's family alike).
6. Patients often aspirate if they vomit while wearing the mask.
7. The mask cannot be used during facial surgery due to intrusion into the sterile field.
8. The mask cannot be worn if the patient has facial injuries such as burns.
9. Skin irritation is often found from the plastic.
10. The face mask does not effectively fit all sizes and shapes of face. Often the soft plastic masks are delivered in a deformed fashion.
11. The face mask usually necessitates clipping the oxygen delivery tube in front of the patient at the bottom of the mask. This is awkward and inconvenient as it may interfere with a patient's movement.
12. The face mask creates irregular infusion of oxygen by the patient, with exhaled air from the patient being mixed with oxygen in the mask.

Another current approach to oxygen delivery to a patient employs an oxygen delivery tube with tubular open ended nasal prongs or cannulae, at the delivery end of the tube, for insertion into a patient's nasal passages. Disadvantages of nasal cannulas include:

1. The patient may not be a nose breather.
2. Sinus irritation of the patient.
3. Patients find the front oxygen cord, necessary with nasal cannulas, difficult to handle as it hangs down directly in front of them and applies downward pressure on their ears, where the cord is again suspended, as in the case of masks.

Of background interest is U.S. Pat. No. 4,593,688 of Payton issued Jun. 10, 1986, which describes and illustrates a tubular system for, example, delivering nebulized oxygen enriched fog or the like to the face and mouth of a croup patient, the tube being suspended, at its delivery end, from a series of straps secured about a patient's head. A portion of the tube is mounted on a pivoting, unshaped frame member so that the tubing is held in front of and below the patient's face, for delivery of the nebulized oxygen enriched fog. The gas delivery to the nose and mouth area of the patient is through orifices in the tube, near the patient's nose and mouth when the tube is in position. This system is intended for children, and would be uncomfortable and restrictive to one's movements, if placed in position on a patient for a long period of time.

Also of background interest is U.S. Pat. No. 6,065,473 issued May 23, 2000 of McCombs et al. This reference describes and illustrates an oxygen delivery system for non-medical uses, for instance in oxygen bars or for oxygen enhancing during exercises such as aerobics or weight lifting. The system comprises a re-usable headset and a conduit to direct oxygen from a source to a headset and to a region proximate to the user's nose and mouth. The conduit is supported by a delivery arm which is preset to a predetermined distance from a user's head for proper supply of oxygen to the user's nose and mouth area.

Also relevant is Knoch et al U.S. Pat. No. 5,575,282 issued Nov. 19, 1996, which describes and illustrates a distribution system for oxygen to a patient's nose and mouth. This system includes a helix for mixing and spirally delivering oxygen towards the patient.

It is an object of the present invention to provide a lightweight system for delivery of oxygen to a patient, which avoids many of these problems of conventional masks and nasal cannulae, and which is suited for medical use.

SUMMARY OF THE INVENTION

In accordance with the present invention there is provided a lightweight oxygen delivery system for a patient, comprising a curved resilient headband to extend between ends from side to side over a patient's head and to be comfortably seatably engaged thereon. An elongated rigid sleeve is provided, a first end of which is pivotably mounted to an outward facing surface of the headband near an end thereof, to rotate with respect to the headband and thereby permit use of the system on either side of a patient's head. An elongated tubular boom is secured within a second end of the sleeve to extend from that end of the sleeve when in operation to terminate at a free end thereof located at a space in front of, and proximal to, the patient's nose and mouth. An oxygen diffuser is positioned at the free end of the tubular boom. The diffuser comprises a body having sides circumscribing a base. The sides form walls defining an interior surface of generally concave configuration, when in operation to direct flow of oxygen generally towards the patient's mouth and nose through the diffuser from an outlet positioned in the base and communicating with the tubular boom. In operation, oxygen is delivered from the boom to the space in the vicinity of the patient's nose and mouth. The sleeve is constructed so as to hold securely an oxygen delivery tube from an oxygen source in fluid communication with the corresponding end of the tubular boom when in operation so as to deliver oxygen from the source to the tubular boom for discharge through the diffuser.

In a preferred embodiment, the elongated tubular boom is secured within the sleeve so as to be telescopically longitudinally adjustable with respect to the sleeve, to facilitate proper location of the diffuser during operation.

The system of the present invention, as will be described in more detail subsequently, avoids many of the problems inherent with conventional medical oxygen delivery systems such as face masks and nasal cannulae. It has no facial contact and allows both nose and mouth breathing preferences with more efficient oxygen delivery.

BRIEF DESCRIPTION OF THE DRAWINGS

These and other advantages of the invention will become apparent upon reading the following detailed description and upon referring to the drawings in which.

Figure 1:
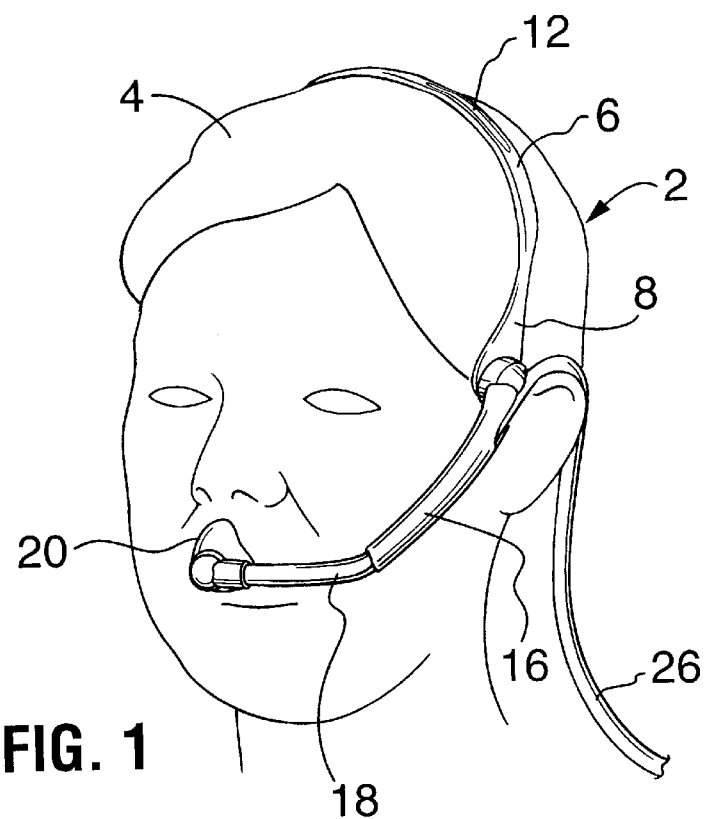
FIG. 1 is a perspective view of an oxygen delivery device according to the present invention mounted on the head of a patient.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAILED DESCRIPTION OF THE PREFERRED EMBODIMENTS

In the following description, similar features in the drawings have been given similar reference numerals.

Figure 4:
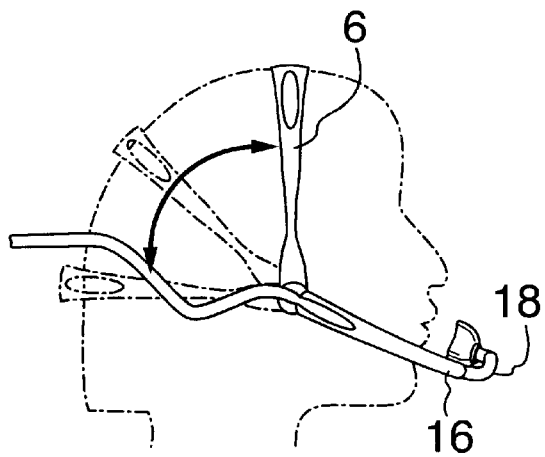
FIG. 4 is a schematic side view of the device of FIG. 1 on a wearer's head, illustrating the adjustability of the headband.

Turning to FIG. 1, there is shown a lightweight delivery system 2, in accordance with the invention, mounted on the head 4 of a patient. The system comprises a curved resilient headband 6 which is of a sufficient size to fit most heads without exerting too much pressure. The headband has widen ends 8 which gently grip the patient's head, spreading the pressure over these widen ends, so as to hold the headband set in position when on a patient's head. The inner surfaces of ends 8 are provided with inwardly extending ridges 10 (FIG. 5) which facilitate the gripping action. As well, apertures 12 in the wider upper portion 14, by capturing some of the patient's hair (where the patient has hair) within, further assist in maintaining the head set in a particular position against unintended dislodgement on a patient's head. The headband is for example made of stiff nylon which gives good tensile strength and resiliency. FIG. 4 illustrates various positions and the range of positions, for headband 6 to be operatively positioned on a patient's head.

Figure 6:
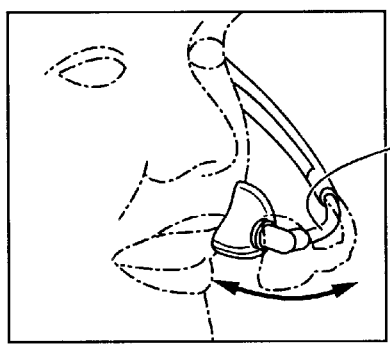
FIG. 6 is a partial view of the boom of the device when worn on a patient, illustrating its positioning flexibility.
Figure 5:
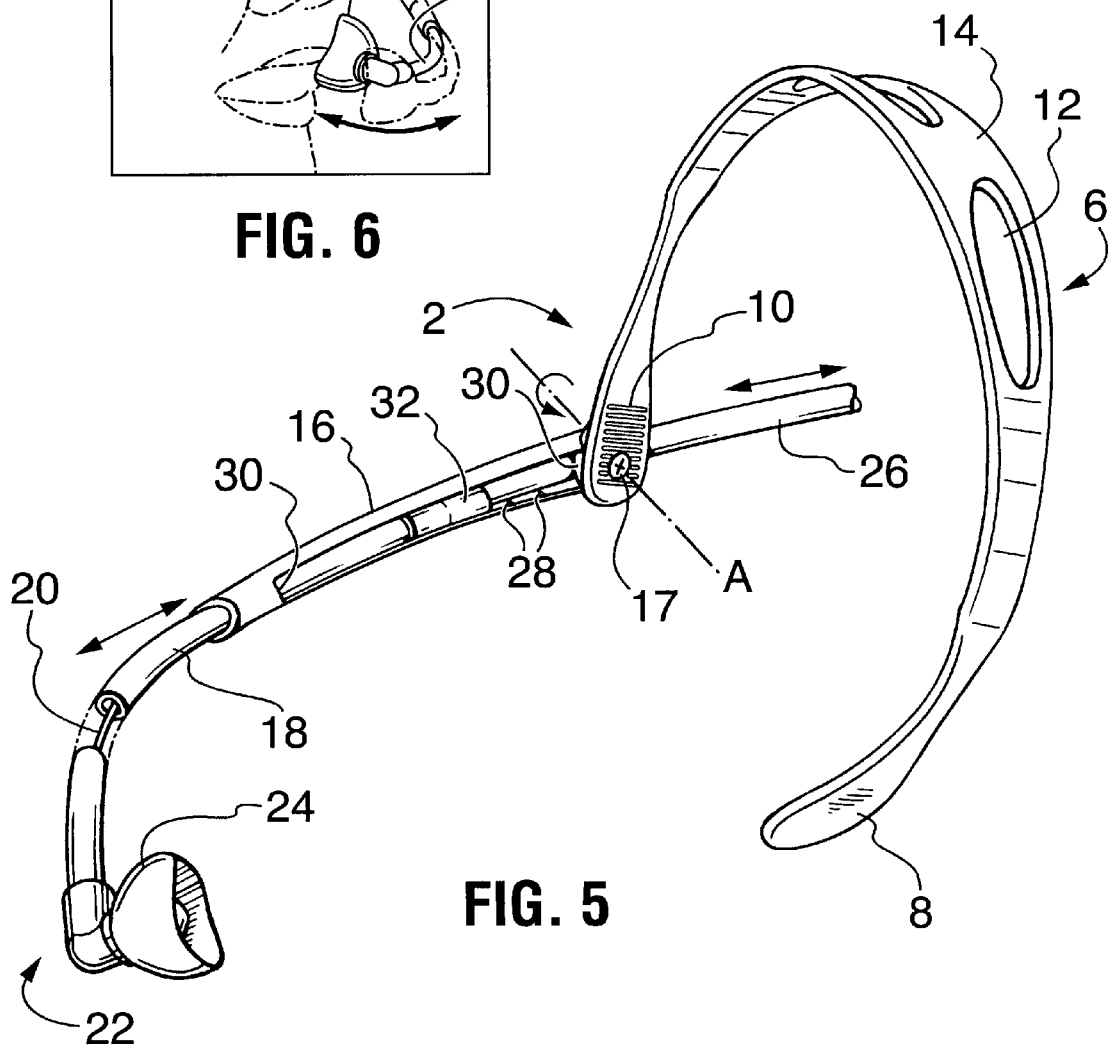
FIG. 5 is a perspective view of the device of FIG. 1 showing the sleeve, boom and oxygen inlet tube.

To one of the widened ends 8 of headband 6 is pivotably secured at pivot connection 17 a sleeve 16. This pivoting occurs about axis A as illustrated (FIG. 5) extending laterally through the upper end of sleeve 16 and associated headband 6. This pivoting motion permits the headband to have the range of motion illustrated in FIG. 4, relative to the sleeve, and further enables the sleeve to be pivoted 180° to convert the system from a left hand one, as illustrated in FIG. 1, to a right hand one, as illustrated in FIG. 5. This pivot is illustrated as being a screw. Alternatively, other conventional pivot means may be used. As well, although not illustrated, it is envisaged that headband 8 may be provided with detachable securing means for sleeve 16, 50 that sleeve 16, boom 18 and diffuser 24 may be replaced on a particular headband 8. Longitudinally slidably secured in sleeve 16 is a tubular boom 18 which extends downwardly and forwardly to end, as illustrated, at a space in the vicinity of the patient's nose and mouth. Boom 18 is preferably a plastic tube in which is embedded a positioning wire 20 (shown in breakaway in FIG. 5) which enables the tube to be bent into an appropriate shape to position the lower end 22 of boom 18 appropriately for delivery of oxygen to the patient, and to be held in that position, as illustrated in FIG. 6.

Figure 3:
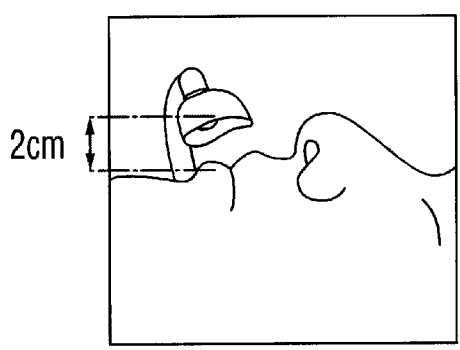
FIG. 3 is a side view of the diffuser of the device of FIG. 1 in position in front of the face of a wearer.

At this lower end 22 of boom 18 is secured an oxygen diffuser 24 through which oxygen, fed to boom 18, is passed into the space in front of the patient's nose and mouth. It is preferred that the distance between the patient's face and the diffuser be about 2 cm (or less), as can be seen in FIG. 3. Diffuser 24 is constructed so as to allow for administration of the oxygen flow to the patient without the patient feeling a direct flow of air onto his or her face. From an appropriate oxygen source (not illustrated), an oxygen delivery tube 26 extends and is connected to the upper end of boom 18 within sleeve 16 for fluid communication with boom 18. Oxygen delivery tube 26 is preferably frictionally engaged within clip portions 28 of sleeve 16. In operation however, relative longitudinal movement of boom 18 and oxygen delivery tube 26 are permitted, with respect to sleeve 16, as illustrated in FIG. 5, thereby assisting in the proper locating of diffuser 24 with respect to the patient's face, irrespective of the size or shape of the patient's head. The limits of this longitudinal movement can be determined by appropriate positioning of stops 30 on sleeve 16 which for example bear against ends of outwardly extending portion 32 of the inner end of boom 18.

Figure 2:
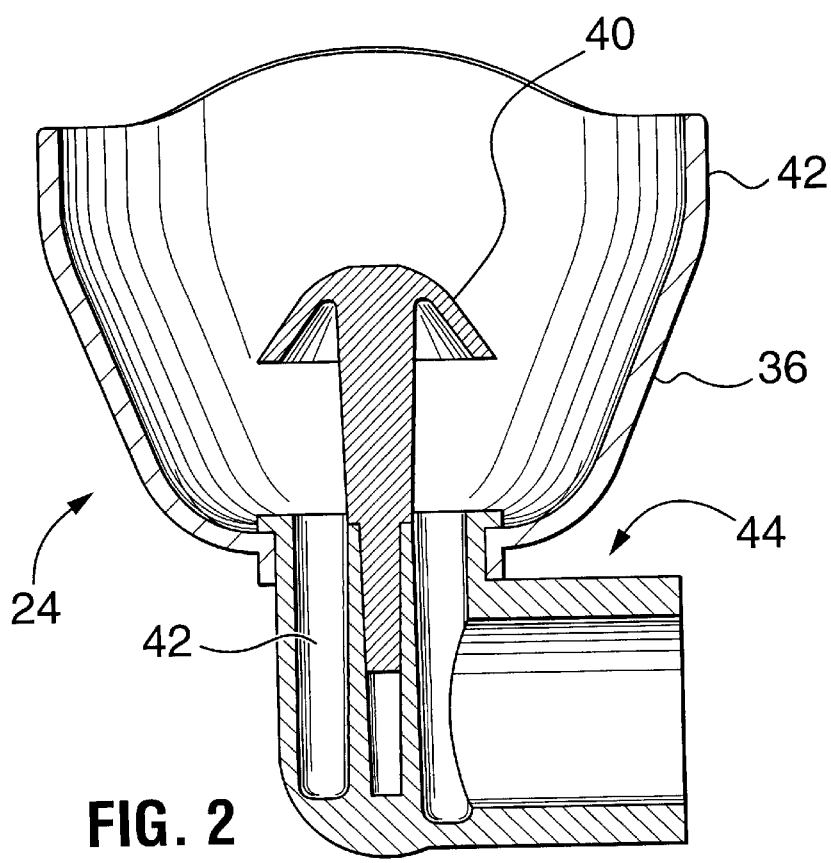
FIG. 2 is a section view of the diffuser of the device of FIG. 1.

The avoidance of a direct flow of air from boom 18 onto the patient's face, through diffuser 24, can be understood from the section view of the diffuser in FIG. 2. Its body 36 has an interior surface of generally concave configuration, circumscribes the oxygen outlet end of boom 18 and directs the flow of oxygen generally towards the patient's mouth and nose when the diffuser 24 is properly positioned and operational. A mushroom-shaped baffle 40 is seated over oxygen outlet 42 of boom 18 so as to assist in the diffusion of oxygen and avoid a direct flow of oxygen towards the patient's face. Baffle 40 impedes oxygen flow from the rear of the body 36 inducing a transmission of that flow from jet to turbulent flow. The shapes of the baffle 40 and body 36 directly influence the mixing characteristics between pure oxygen stream and the ambient air (containing approximately 21% oxygen by volume), and thus determine the oxygen content of the plume of oxygen-enriched air delivered from the diffuser to the surface of the patient's face.

As well, body 36 of diffuser 24 has a contoured inner surface, forming a somewhat triangular cup shape which follows the shape of the nose/mouth nexus of a patient, thereby forming a shaped plume of oxygen-enriched air in front of the patient's face. The enclosed volume of that cup may be modified to accommodate a larger plume and increase the total oxygen delivered during respiratory inspiration. As can be seen in FIG. 2, the wall of body 36 near outer rim 42 of body 36 becomes more "vertical" (with opposite sides being parallel) than outwardly extending, as are the lower portions of the body. This shaping of the rim edges of the body permits a concentrating of oxygen and a shaping of the plume, providing a more precise direction of the plume of oxygen-enriched air towards the patient's nose/mouth. The body 36 of diffuser 24 swivels about end 44 of boom 18 to enable proper orienting of the diffuser when the boom is either in left hand or right hand mode.

Of course the overall shaping of body 36 and baffle 40 may be modified to suit the requirements of a particular application or user need.

There are many obvious advantages of the present system, for delivery of oxygen to a patient, over prior art devices, including the lack of facial contact of the present system, the elimination of the possibility of the patient aspirating should the patient be ill during oxygen therapy, the fact that it allows both nose and mouth breathing preferences and the deflection of oxygen flow away from the face of the user during absence of inhalation, for increased patient comfort. As well, the system according to the present invention enables a patient to eat or speak in an unobstructed manner.

The system according to the present invention permits the headband 6 to be adjusted to be clear of any particular area on a patient's head and adjust for a wide range of patient sizes.

Figure 8A:
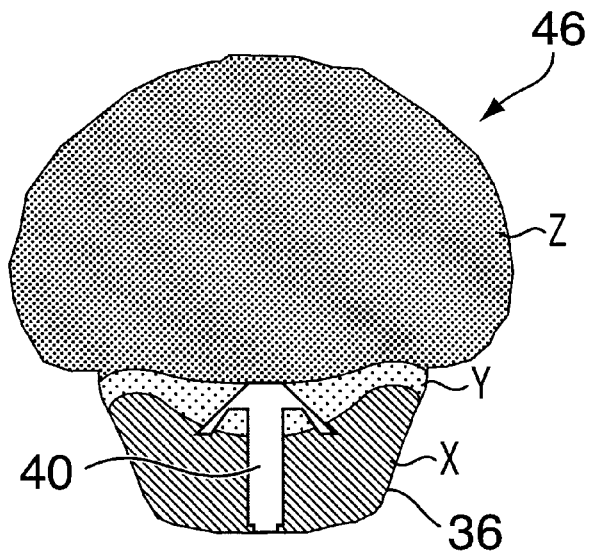
FIGS. 8A and 8B are schematic views, from the side, showing the concentration of oxygen in the air around the diffuser body during operation of the system, respectively when the patient is not inhaling, and when the patient inhales.
Figure 8B:
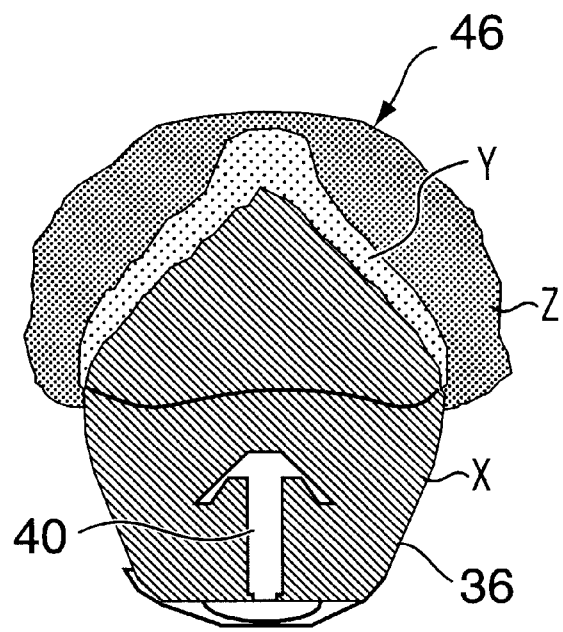

As can be seen in FIGS. 8A and 8B, a plume 46 of oxygen enriched air leaves the diffuser. In operation, this plume will be in the vicinity of the patient's nose and mouth area. When the patient is not inhaling (FIG. 8A), the areas of highest increased oxygen concentration X in plume 46 remain in and near diffuser body 36 with the areas Y of moderately increased oxygen concentration and areas Z of lowest increased oxygen concentration extending outwardly from diffuser body 36 as illustrated. When the patient inhales, as seen in FIG. 8B, the areas X and Y of highest and moderate increased oxygen concentrations are drawn towards the patient's mouth and nose area, making these increased oxygen concentrations available to be inhaled by the patient.

Figure 7:
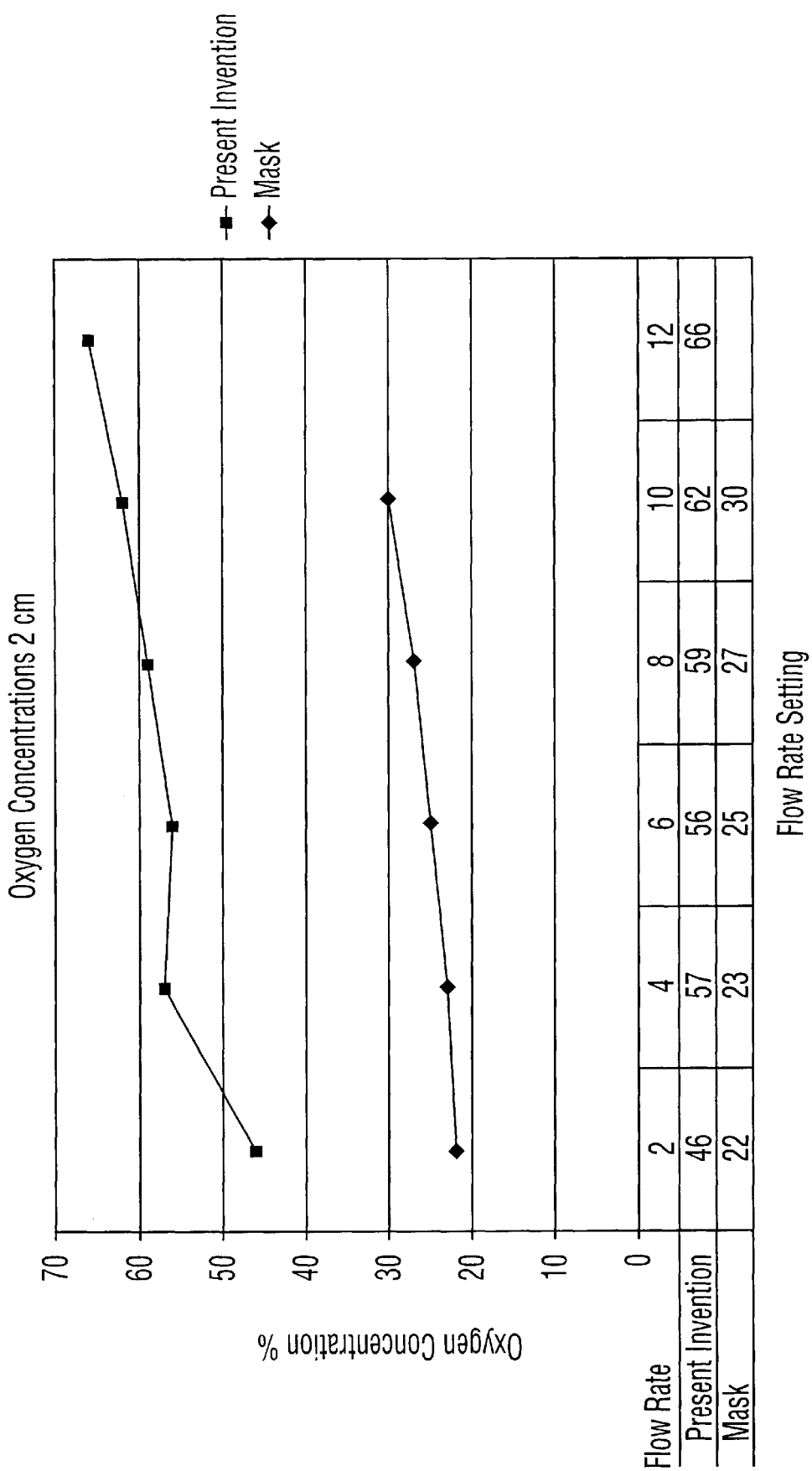
FIG. 7 is a graph illustrating oxygen concentrations delivered to patient's in percentages, based on flow rate settings, of the device of FIG. 1 when situated at a distance of 2 cm from a wearer's face, when compared to oxygen concentrations delivered by a conventional oxygen mask

In clinical test results which are illustrated in the graph of FIG. 7, the actual oxygen concentration for a 2 cm distance of the diffuser 24 of applicant's device from a patient's face ranges between 46% at a flow rate setting of 2 (approximately liters per minute) to 66% at a flow rate setting of 12 (approximately liters per minute), as compared to an oxygen concentration delivery of between 22% and 30% for flow rate settings of from 2 to 10 in a conventional oxygen mask. Thus, higher concentrations of oxygen can be delivered to a patient, using the system of the present invention, at lower oxygen flow rates, and with conventional face masks, providing a significant saving in oxygen.

Advantages of the present system, for delivery of oxygen to a patient, over prior art devices, include the facts:

the possibility of the patient aspirating is eliminated should they be ill during oxygen therapy, it is lightweight, it does not give the patient the feeling of being sick, instead it has a high tech look that is positive for the patient, it allows for the sampling and monitoring of expired carbon dioxide directly at the boom end, oxygen tubing comes off at the side instead of directly at the bottom of the mask as seen in traditional mask devices, making it easier for nursing staff to handle, the device does not outgas as often happens with full face masks, there is no smell of plastic, there is no need to remove oxygen therapy while patient is eating or speaking, it is well tolerated by patients; it provides comfort not found with traditional devices, it could be reused for a longer period of time than conventional masks and nose cannula systems, it allows for the administration humidified air as well as non-humidified air, one size adjusts for a wide range of patient sizes, it is effective whether the patient is a mouth or nose breather, it permits adjusting to be clear of any particular area on a patent's head.

The oxygen delivery system of the present invention is envisaged as having particular application where a patient has his/her faculties and is not in a state where the headband might be unintentionally dislodged, or the diffuser and associated boom might be unintentionally displaced from normal, operative position.

As for children, this population traditionally does not tolerate mask oxygen therapy. The device according to the present invention is not only likely to be considered to be stylish by older children, it also could support decorations to represent popular cartoon characters, or the like, to appeal to younger children.

Thus, it is apparent that there has been provided in accordance with the invention a lightweight oxygen delivery system that fully satisfies the objects, aims and advantages set forth above. While the invention has been described in conjunction with an illustrated embodiment thereof, it is evident that many alternatives, modifications and variations will be apparent to those skilled in the art in light of the foregoing description. For example, a multi lumena boom 18, instead of one having a single tube, may be provided, each tube having a distinct function. Accordingly, it is intended to embrace all such alternatives, modifications and variations as fall within the spirit and broad scope of the invention.

What we claim as our invention:

1. A lightweight oxygen delivery system for a patient comprising:

(a) a curved resilient headband to extend between ends from side to side over a patient's head and to be comfortably seatably engaged thereon;

(b) an elongated rigid sleeve, a first end of which is pivotably mounted to an outward-facing surface of the headband near one end thereof, to rotate with respect to the headband and thereby permit use of the system on either side of the patient's head;

(c) an elongated tubular boom secured within a second end of the sleeve to extend from that end of the sleeve when in operation to terminate at a free end located at a space in front of, and proximal to, a nose and mouth of the patient;

(d) an oxygen diffuser at said free end of the boom, through which diffuser oxygen may be delivered from the boom to the space in the vicinity of the patient's nose and mouth; the diffuser comprising a body having sides circumscribing a base, the sides forming walls defining an interior surface of generally concave configuration, wherein the interior surface is of somewhat triangular, cup shape to follow a shape of a nose/mouth nexus of the patient when in position on the patient, when in operation to direct flow of oxygen generally towards the patient's mouth and nose through the diffuser from an outlet positioned in the base and communicating with the tubular boom;

the sleeve, constructed so as to hold securely an oxygen delivery tube from an oxygen source in fluid communication with the corresponding end of the tubular boom so as to deliver oxygen from the oxygen source to the tubular boom for discharge through the diffuser.

2. A system according to claim 1, wherein the tubular boom is secured within the sleeve for telescopic, longitudinal adjustment of the tubular boom with respect to the sleeve to facilitate positioning of the oxygen diffuser with respect to a nose and mouth of a patient.

3. A system according to claim 2, wherein stop means are provided within the sleeve to limit the telescopic adjustment of the tubular boom with respect to the sleeve between two longitudinal extremities.

4. A system according to claim 2, wherein a wire is embedded in the tubular boom to permit bending of the tubular boom to a particular shape and maintaining of that shape.

5. A system according to claim 2, wherein the diffuser comprises a body having an interior surface of generally concave configuration, when in operation to direct flow of oxygen generally towards a patient's mouth and nose through a diffuser port.

6. A system according to claim 1, wherein interior walls of the sleeve are formed so as to frictionally engage a portion of the oxygen delivery tube when in operation.

7. A system according to claim 1, wherein the ends of the headband are widened.

8. A system according to claim 7, wherein interior surfaces of the widened ends of the headband are provided with inwardly extending ribs to assist in frictionally engaging a patient's head when the headband is in position.

9. A headband according to claim 7, wherein the headband is constructed so as to be of a size and shape to enable it to be fit both over or behind a patient's head when ends of the headband are in position on a patient's head.

10. A headband according to claim 7, wherein intermediate portions of the headband are provided with apertures through which a patient's hair may extend, to further facilitate holding the headband in position on a patient's head and prevent the headband from becoming dislodged.

11. A system according to claim 7, wherein the interior surface is of somewhat triangular, cup shape to follow a shape of a nose/mouth nexus of a patient when in position on a patient.

12. A system according to claim 1, wherein the tubular boom is constructed so as to be bendable to a particular shape to facilitate positioning of the tubular boom with respect to a patient's nose and mouth.

13. A system according to claim 12, wherein a wire is embedded in the tubular boom to permit bending of the tubular boom to a particular shape and maintaining of that shape.

14. A system according to claim 1, wherein the diffuser further comprises a baffle seated over the diffuser outlet so as to assist in mixing of oxygen with ambient air and avoid a direct flow of oxygen towards a face of a patient.

15. A lightweight oxygen delivery system for a patient comprising:

(a) a curved resilient headband to extend between ends from side to side over a patient's head and to be comfortably seatably engaged thereon;

(b) an elongated rigid sleeve, a first end of which is pivotably mounted to an outward-facing surface of the headband near one end thereof, to rotate 360° with respect to the headband;

(c) an elongated tubular boom secured within a second end of the sleeve to extend from that end when in operation to terminate at a free end located at a space in front of, and proximal to a nose and mouth of a patient;

(d) an oxygen diffuser at said free end of the tubular boom, through which diffuser oxygen may be delivered from the boom to the space in the vicinity of the patient's nose and mouth; the diffuser comprising a body having sides circumscribing a base, the sides forming walls defining an interior surface of generally concave configuration, when in operation to direct flow of oxygen generally towards the patient's mouth and nose communicating with the tubular boom;

the sleeve, constructed so as to hold securely an oxygen delivery tube from an oxygen source in fluid communication with the corresponding end of the tubular boom when in operation so as to deliver oxygen from the oxygen source to the tubular boom for discharge through the diffuser, the tubular boom being secured within the sleeve for telescopic, longitudinal adjustment of the tubular boom with respect to the sleeve to facilitate positioning of the oxygen diffuser with respect to the patient's nose and mouth.

16. A system according to claim 15, wherein the tubular boom is constructed so as to be bendable to a particular shape to facilitate positioning of the tubular boom with respect to nose and mouth of a patient.

17. A system according to claim 15, wherein the diffuser further comprises: a baffle seated over the diffuser outlet so as to assist in mixing of oxygen with ambient air and avoid a direct flow of oxygen towards a face of a patient.

* * * * *